United States Patent [19]

McKillop et al.

[11] Patent Number: 5,214,192
[45] Date of Patent: May 25, 1993

[54] PROCESS FOR PREPARING IODOARENE COMPOUNDS

[75] Inventors: Alexander McKillop, Norwich; Duncan Kemp, High Crompton, both of England

[73] Assignee: Interox Chemicals Limited, London, England

[21] Appl. No.: 768,281

[22] PCT Filed: Feb. 28, 1990

[86] PCT No.: PCT/GB90/00314
§ 371 Date: Oct. 2, 1991
§ 102(e) Date: Oct. 2, 1991

[87] PCT Pub. No.: WO90/09982
PCT Pub. Date: Sep. 7, 1990

[30] Foreign Application Priority Data

Mar. 2, 1989 [GB] United Kingdom ............... 8904800

[51] Int. Cl.$^5$ .............................................. C07C 67/00
[52] U.S. Cl. ..................................... 560/131; 560/138; 560/139; 560/142
[58] Field of Search ................ 560/131, 138, 139, 142

[56] References Cited

U.S. PATENT DOCUMENTS

| | | | |
|---|---|---|---|
| 3,644,486 | 2/1972 | Boldt et al. | 560/131 |
| 3,772,383 | 11/1973 | Kominami et al. | 560/131 |
| 3,887,608 | 6/1975 | Kominami et al. | 560/131 |

*Primary Examiner*—José G. Dees
*Assistant Examiner*—Vera C. Clarke
*Attorney, Agent, or Firm*—Larson and Taylor

[57] ABSTRACT

Diacetoxyarene compounds are obtained by reacting a perborate such as sodium perborate monohydrate or tetrahydrate and acetic acid with an iodoarene compound under mild conditions, such as 40 to 50° C. The iodoarene can be further substituted by a wide range of substituents, such as halo, nitro, alkyl, alkoxy or carboxylic acid, in any position around the nucleus, except that electron withdrawing substituents occupy meta positions only. The invention process thus enables a wide range of substituted diacetoxyarene compounds to be produced using widely available and easily handled materials under mild operating conditions.

8 Claims, No Drawings

PROCESS FOR PREPARING IODOARENE COMPOUNDS

The present invention relates to the preparation of iodo compounds and more specifically to the preparation of diacetoxyiodoarene compounds.

Diacetoxyiodoarene compounds are examples of polyvalent iodo compounds that have specific practical uses in organic syntheses, acting for example by way of ligand exchange or as specific oxidants.

When commercial scale activities are contemplated, it is generally recognised that in an ideal world, it would be advantageous to employ reactants, for example oxidising systems that were not only widely available, storage stable, easy to handle and relatively cheap, but would also perform the desired reaction under mild conditions.

It is an object of the present invention to provide a process for the preparation of diacetoxyiodoarene compounds that employs widely available and relatively cheap reagents and which can be carried out under relatively mild conditions.

According to the present invention, there is provided a process for the preparation of an diacetoxyiodoarene compound in which an iodoarene compound is brought into contact with an excess of alkali metal perborate and acetic acid at a mild temperature and permitted to react until at least a proportion of the iodoarene has been oxidised to the corresponding diacetoxyiodoarene.

The iodo arene can be otherwise unsubstituted or be substituted by one or more of a wide range of substituents, which can be either electron donating or electron withdrawing, provided that the latter is meta to the iodo group. It will be understood that electron-withdrawing substituents in either the ortho or para position significantly inhibit the instant invention process. When two or more substituents are present, they can be the same as each other or different. Provided that the foregoing constraint is taken into account, the or each substituent can be chosen from halo, nitro, carboxylic acid, nitrile, alkyl or alkoxy substituents. The halo group can be a fluoro, chloro, bromo or iodo group, and the alkyl substituent preferably contains only a small number of carbon atoms. It will be recognised that if certain other substituents are present, such as an aldehyde, they will also, possibly preferentially, be oxidised under the conditions of the present invention, so that the substrate is oxidised at two substituents. It will be recognised that where a substituent is oxidisable under the conditions of the present invention, the reaction will be influenced not only by the the electron-withdrawing or donating nature of the sutstituent itself, but also by that of the corresponding oxidised substituent. Thus, for example, the reaction product of an aldehyde substituent is a carboxylic acid substituent, and accordingly irrespective of whether there would be any constraints imposed by virtue of the aldehyde itself, the nature of its oxidation product means that it can be present only in the meta position to the iodo substituent.

In many instances the arene nucleus is benzene, although di or polycyclic nuclei are also suitable It will also be understood from the foregoing since iodo is a halo group that it is possible for the arene nucleus to be substituted by two or more iodo groups, in any positions around the nucleus. Naturally, though, constraints applicable to the positioning of any substituent relative to an iodo group are applied in respect of each iodo group Advantageously, provided that the substituents are suitably chosen position-wise in accordance with their electron donating or withdrawing nature, there appears to be no significant restriction on the number of substituents around the arene nucleus, other than the number of available carbon atoms in the nucleus. Thus, for example, up to four substituents in addition to the iodo substituent can easily be contemplated around a benzene nucleus, if desired The alkali perborate is particularly conveniently a sodium perborate on account of its bulk availability and excellent storage and handling properties of the two industrially available products sodium perborate monohydrate and sodium perborate tetrahydrate, which have respectively the empirical formulae $NaBO_3.H_2O$ and $NaBO_3.4H_2O$, though these do not properly represent the structure of the compounds. Whilst there are various ways in which the compound can be introduced into the reaction medium, a particularly safe way comprises introducing it progressively, such as in small portions or continuously during an introductory period, either at or below the desired reaction temperature.

The invention reaction conditions for the oxidation of the iodoarene prefer a substantial excess of perborate to be employed, and especially a mole ratio in excess of 5:1 perborate:iodoarene and particularly from 5:1 to 15:1. Naturally, there is some variation in the efficiency of the reaction depending upon which substituents are present, but by appropriate selection of conditions, it is possible to obtain very high conversion to the diacetoxyiodoarene at a mole ratio chosen within the aforementioned ranges.

The reaction medium comprises glacial acetic acid. Selection of acetic acid is critical, in that the cooresponding set of reactions using related carboxylic acids, such as propionic acid or trifluoracetic acid appear to be significantly inhibited under the process conditions in which acetic acid is very effective.

The concentration of substrate in the reaction medium can be selected within a very wide range, for example from 0.05M to a saturated solution.

The reaction is carried out at a mild temperature, by which is meant that there is no need to maintain a high temperature during the reaction or even approach closely reflux temperature for the medium. In many instances, it is convenient to employ a temperature that is above ambient, and preferably above 35° C., up to about 70° C. Very effective oxidations have been achieved in the region of or around 40° to 50° C. throughout the reaction period.

The precise mechanism for the present invention is open to discussion at present. It is speculated that there may be some mode or modes of interaction between the perborate oxidant and the reaction medium which can result in the generation in situ of one or more active species that is or are responsible for the effective oxidation reaction rather than direct interaction of either with the substrate. It will be recognised, though, that the present invention stands by virtue of its demonstrated results and not by the truth or otherwise of any particular point of speculation.

The total reaction period will usually be determined in practice by taking into account the reaction temperature and the substrate and will often include a period during which perborate is introduced and a subsequent period in which the reaction is allowed to progress The perborate introduction period is often chosen within the range of 10 to 60 minutes although a longer period of introduction such as up 80% of the total reaction period, or even longer, is a reasonable alternative, because reaction can also occur whilst the perborate is being introduced. The total reaction period is often selected in the range of from 3 to 12 hours, and for many substrates from 4 to 7 hours.

The reaction can be monitored, for example by thin layer chromatography and recovery of the product commenced when the monitoring indicates that either a desired proportion of the substrate has been converted to the product, or the reaction rate has slowed thereby indicating that little further product could be obtained. In practice, reaction periods can be gauged in small scale trials and refined in bulk-scale operation.

The invention process is particularly suitable for a batch style reaction procedure, but it will be recognised that by a suitable choice of reactor design such a tubular once through reactor, it is a practical proposition to carry out the reaction continuously, especially for those substrates that employ a relatively short reaction period The product can be recovered from the reaction mixture by removal of at least part of the reaction medium and preferably all of it, such as by evaporation, preferably under reduced pressure, and subsequent addition of water to the residue, thereby causing formation of a solid product. A suitable amount of water is often chosen in the range of 0.5 to 5 parts v/v per part of reaction mixture remaining after the evaporation step. The solid can then be separated using convention solid/liquid separating techniques such as centrifugation, filtration or settling The aqueous residue comprises a saturated solution of the product. Accordingly, a further amount of product can be recovered by subsequently contacting the aqueous residue with a suitable solvent, for example a haloalkane such as chloroiorm or a similar solvent preferably having a low boiling point and immiscibility with water, separating the two phases and removing the solvent, such as by evaporation, preferably under reduced pressure A convenient ratio of stripping solvent to aqueous residue is often chosen in a total v/v ratio of 1:1 to 3:1. The conventional techniques of solvent stripping, viz continuous co or counter-current contact or multiple batch contact are applicable.

It will also be recognised that product losses can be reduced additionally to the solvent stripping technique or alternatively instead of that technique by recycling the aqueous residue, either before or after its contact with the above-mentioned solvent, in place of at least a fraction of the water that is added to the reaction mixture residue in an early phase of the product recovery Having described the invention in general terms, specific embodiments will now be described more precisely by way of non-limiting example only

EXAMPLES 1 to 15

Each of these Examples was carried out using the following general procedure. A substrate identified in the Table as ArI, $10^{-2}$ moles, was dissolved in glacial acetic acid, 90 mls. The solution was stirred and maintained at about 40–45 during the addition of sodium perborate tetrahydrate, $1.2 \times 10^{-2}$ moles, in small portions over a period of 20 minutes and throughout the subsequent reaction period. The progress of the reaction was monitored by withdrawing a number of small samples from the reaction mixture at intervals for immediate analysis by thin layer chromatography. The reaction was allowed to continue until the analyses indicated that the substrate had been consumed. This varied from about 4 hours for iodobenzene up to as long as 8 hours for 3-trifluoromethyliodobenzene. The reaction mixture volume was reduced by about half by evaporation of acetic acid under reduced pressure and then water, 50 mls, was added to the residue. The solid which separated out, crude product, was recovered by filtration, and dried in air. The filtrate was contacted with chloroform 3×25 mls portions, and the combined organic phase was dried with anhydrous magnesium sulphate, and evaporated under reduced pressure, thereby precipitating a further amount of crude product. The two crude products were combined, recrystallised and dried to provide the yield given in the Table, which is the molar percentage of purified diacetoxyiodoarene product, based on the substrate present initially. The identity of the product was subsequently confirmed by melting point comparison with the reading given in the literature and by infra red spectral analysis.

THE TABLE

| Example no. | Iodoarene | % Yield of diacetoxyiodoarene |
| --- | --- | --- |
| 1 | $C_6H_5I$ | 80 |
| 2 | $2\text{-}CH_3C_6H_4I$ | 73 |
| 3 | $4\text{-}CH_3C_6H_4I$ | 66 |
| 4 | $2,4\text{-}(CH_3)_2C_6H_3I$ | 75 |
| 5 | $2,6\text{-}(CH_3)_2C_6H_3I$ | 75 |
| 6 | $2,4,6\text{-}(CH_3)_3C_6H_2I$ | 77 |
| 7 | $2,3,5,6\text{-}(CH_3)_4C_6HI$ | 71 |
| 8 | $4\text{-}ClC_6H_4I$ | 73 |
| 9 | $2,5\text{-}Cl_2C_6H_3I$ | 76 |
| 10 | $4\text{-}IC_6H_4I$ | 80 |
| 11 | $3\text{-}CF_3C_6H_4I$ | 71 |
| 12 | $3\text{-}CH_3OC_6H_4I$ | 73 |
| 13 | $4\text{-}CH_3OC_6H_4I$ | 75 |
| 14 | $3\text{-}NO_2C_6H_4I$ | 80 |
| 15 | $1\text{-}C_{10}H_7I$ | 76 |

COMPARISONS C16 to C27

When Example 14 was repeated, but using either the 2- or 4-nitroiodobenzene in comparisons C16 and C17, and when Example 11 repeated but using either 2- or 4 trifluoromethyliodobenzene in comparisons C18 and C19, substantially no production of the diacetoxyiodoarene compound was detected. Similarly, in comparisons C20 and C21 when the starting material comprised 2- or 4-iodobenzoic acid, in comparisons C22 and C23 when the starting material comprised ethyl 2- or 4-iodobenzoate and in comparisons C24 and C25 when the starting material comprised 2- or 4-iodobiphenyl, all otherwise employing the general conditions of Example 1, substantially no diacetoxyiodoarene compound was detected The results from the Examples and comparisons demonstrate clearly that the invention process can be carried out effectively in the presence of an electron-donating substituent in any position and an electron-withdrawing substituent in the meta (3-) position, but that the desired reaction is inhibited by an electron-withdrawing substituent in the ortho or para (2- or 4-) positions.

When Example 1 was repeated, but using propionic acid or trifluoroacteic acid in comparisons C26 and C27, instead of acetic acid, iodobenzene was recovered, unreacted. This indicates that the selection of acetic acid is a critical element in the reaction process, in that substitution even by closely related aliphatic carboxylic acids seems to prevent oxidation of the iodo substituent.

We claim:

1. A process for the preparation of a diacetoxyiodoarene compound by reaction between an iodoarene compound and a donor of acetoxy groups in the presence of an oxidising agent, wherein an unsubstituted or substituted iodoarene compound is brought into contact with an excess of alkali metal perborate and acetic acid at a mild temperature and permitted to react until at least a proportion of the iodoarene has been oxidised to the corresponding diacetoxyiodoarene, provided that any electron-withdrawing substituent is meta to the iodo substituent.

2. A process according to claim 1 wherein the iodoarene compound comprises an iodo substituted benzene or di or polycyclic arene nucleus that is further substituted by 0 to 4 additional substituents.

3. A process according to claim 1 or 2 wherein the iodoarene compound is substituted by at least 1 substituent selected from the group consisting of halo, nitro, carbosylic acid, nitrile, alkyl and alkoxy groups.

4. A process according to claim 1 or 2 wherein the alkali metal perborate is selected from the group consisting of sodium perborate monohydrate and tetrahydrate.

5. A process according to claim 1 or 2 wherein an alkali metal perborate is employed in a mole ratio to the iodoarene of from 5:1 to 15:1.

6. A process according to claim 1 or 2 which the reaction temperature is in the range of from 35° to 70° C.

7. A process according to claim 1 or 2 which the reaction period is in the range of 3 to 12 hours.

8. A process according to claim 1, wherein an iodoarene compound substituted by at least one substituent selected from the group consisting of halo, nitro, carboxylic acid, nitrile, alkyl, and alkoxy groups is brought into contact with sodium perborate monohydrate or tetrahydrate in a mole ratio of perborate to iodoarene of from 5:1 to 15:1.

* * * * *